US006852312B2

(12) United States Patent
Worley et al.

(10) Patent No.: US 6,852,312 B2
(45) Date of Patent: *Feb. 8, 2005

(54) BIOCIDAL POLYSTYRENE HYDANTOIN PARTICLES

(75) Inventors: Shelby D. Worley, Auburn, AL (US); Yongjun Chen, Auburn, AL (US)

(73) Assignee: Auburn University, Auburn, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/272,264

(22) Filed: Oct. 15, 2002

(65) Prior Publication Data

US 2003/0044377 A1 Mar. 6, 2003

Related U.S. Application Data

(63) Continuation of application No. 09/948,945, filed on Sep. 6, 2001, now Pat. No. 6,548,054.

(51) Int. Cl.[7] .................... A61K 31/785; A61K 31/765; A61K 9/14; A61K 9/16; A01N 25/00
(52) U.S. Cl. ................ 424/78.36; 424/405; 424/78.37; 424/489; 424/497
(58) Field of Search ............................ 424/78.36, 405, 424/78.37, 489, 497, 78.07, 78.01

(56) References Cited

U.S. PATENT DOCUMENTS

| | | |
|---|---|---|
| 2,225,384 A | 12/1940 | Graenacher et al. |
| 3,519,608 A | 7/1970 | Kelley et al. |
| 3,821,098 A | 6/1974 | Garratt et al. |
| 3,931,213 A | 1/1976 | Kaminski et al. |
| 4,000,293 A | 12/1976 | Kaminski et al. |
| 4,349,646 A | 9/1982 | Nudel et al. |
| 4,420,590 A | 12/1983 | Gartner |
| 4,681,948 A | 7/1987 | Worley |
| 4,767,542 A | 8/1988 | Worley |
| 4,842,932 A | 6/1989 | Burton |
| 4,955,392 A | 9/1990 | Sorkin |
| 5,057,612 A | 10/1991 | Worley et al. |
| 5,104,649 A | 4/1992 | Jansson et al. |
| 5,126,057 A | 6/1992 | Worley et al. |
| 5,284,157 A | 2/1994 | Miller et al. |
| 5,338,859 A | 8/1994 | Bhattacharya |
| 5,490,983 A * | 2/1996 | Worley et al. .............. 424/405 |
| 5,561,183 A | 10/1996 | Kwon et al. |
| 5,670,646 A | 9/1997 | Worley et al. |
| 5,756,764 A | 5/1998 | Fenteany et al. |
| 5,785,963 A | 7/1998 | Tseng |
| 5,882,357 A | 3/1999 | Sun et al. |
| 5,889,130 A | 3/1999 | Worley et al. |
| 5,902,818 A | 5/1999 | Worley et al. |
| 5,968,599 A | 10/1999 | Jung et al. |
| 5,981,668 A | 11/1999 | Fujita et al. |
| 6,548,054 B2 * | 4/2003 | Worley et al. ........... 424/78.36 |
| 2002/0051757 A1 | 5/2002 | Clare et al. |

FOREIGN PATENT DOCUMENTS

| | | |
|---|---|---|
| WO | WO 01/07709 A1 | 2/2001 |
| WO | WO 02/06579 A2 | 1/2002 |

OTHER PUBLICATIONS

Sun, Y. and G. Sun, "Novel Regenerable N–Halamine Polymeric Biocides. I. Synthesis, Characterization, and Antibacterial Activity of Hydantoin–Containing Polymers," *J. Appl. Polymer Sci.* 80 :2460–2467 (2001).

U.S. Appl. No. 09/685,963, filed Oct. 10, 2000, inventor S.D. Worley et al.

"Water Absorbing Composition Manufacture" (abstract) [online], Jun. 2000 [retrieved Oct. 4, 2001], retrieved from *West, Derwent World Patents Index* Accession No. 2000–530587.

Asinger, F., et al., "Zur Darstellung von Imidazolidin–Thionen–(4) und Imidazolin–(3)–Thionen–(5)," *Mh. Chem.* 98:338–352, 1967.

Asinger, F., et al., "Zur Kenntnis der Hydrolyse Substituierter Imidazolidin–Thione–(4)," *Mh. Chem.* 98:1843–1851, 1967.

Bellar, T.A., et al., "The Occurrence of Organohalides in Chlorinated Drinking Waters," *J. Am. Waters Works Assoc.* 66:703–706, 1974.

Buchenska, J., "Polyamide Fibers (PA6) With Antibacterial Properties," *J. Applied Polymer Sci.* 61:567–576, 1996.

Chemical Abstract No. 40044, 1968.

Chemical Abstract No. 444909, 1970.

Cho, W.J., et al., "Synthesis and Biocidal Activities of Polymer. II. Bactericidal Activity of Homopolymer of AcDP and Copolymer of AcD With MMA," *J. Macromolecular Sci.—Pure and Applied Chem.* 32(3):479–495, 1995.

Christian, J.D., "4–Imidazolidinethiones," *J. Org. Chem.* 22:396–399, 1957.

DuPont Advertisement, *Chem. Eng. News* 26(6), 1948.

Elrod, D.B., et al., "A Facile Synthetic Approach to Imidazolidinone Biocides," *Ind. Eng. Chem. Res.* 38(11):4144–4149, 1999.

(List continued on next page.)

Primary Examiner—Thurman K. Page
Assistant Examiner—M B Fubara
(74) Attorney, Agent, or Firm—Gardner Groff, P.C.

(57) ABSTRACT

Method for preparing biocidal halogenated polystyrene hydantoins. The biocidal polymers poly-1,3-dichloro-5-methyl-5-(4'-vinylphenyl)hydantoin, poly-1,3-dibromo-5-methyl-5-(4'-vinylphenyl)hydantoin, and their monohalogenated alkali metal salts and protonated derivatives have been prepared as porous beads by use of highly crosslinked polystyrene beads as starting materials. The porous beads will be useful in water and air disinfection applications when employed in cartridge filters and carafes (for water), as well as for controlling noxious odor when mixed with absorbent materials in items such as disposable diapers, incontinence pads, bandages, sanitary napkins, pantiliners, mattress covers, shoe inserts, sponges, animal litter, carpets, fabrics, and air filters or the like.

44 Claims, No Drawings

OTHER PUBLICATIONS

Emerson, D.W., "Polymer–Bound Active Chlorine: Disinfection of Water in a Flow System. Polymer Supported Reagents. 5," *Ind. & Eng. Chem. Res.* 29(3):448–450, 1990.

Emerson, D.W., "Slow Release of Active Chlorine and Bromine From Styrene–Divinylbenzene Copolymers Bearing N,N–Dichlorosulfonamide, N–Chloro–N–Alkylsulfonamide, and N–Bromo–N–Alkylsulfonamide Functional Groups. Polymer–Supported Reagents. 6," *Ind. & Eng. Chem. Res.* 30(11):2426–2430, 1991.

Emerson, D.W., et al., "Functionally Modified Poly(styrene–Divinylbenzene). Preparation, Characterization, and Bactericidal Action," *Ind. & Eng. Chem. Prod. Res. and Dev.* 17(3):269–274, 1978.

Hayes, R.A., "Polymeric Chain Transfer Reactions. Polymerization of Some Vinyl Monomers in the Presence of Vinyl Polymers," *J. Polymer Sci.* XI(6):531–537, 1953.

Hazziza–Laskar, J., et al., "Biocidal Polymers Active by Contact. I. Synthesis of Polybutadiene With Pendant Quaternary Ammonium Groups," *J. App. Polymer Sci.* 50:(4):651–662, 1993.

Hazziza–Laskar, J., et al., "Biocidal Polymers Active by Contact. IV. Polyurethanes Based on Polysiloxanes With Pendant Primary Alcohols and Quaternary Ammonium Groups," *J. App. Polymer Sci.* 58(1):77–84, 1995.

Hoff, J.C., et al., "Comparison of the Biocidal Efficiency of Alternative Disinfectants," *J. Am. Water Works. Assoc.* 73:40–44, 1981.

Kanazawa, A., et al., "Polymeric Phosphonium Salts as a Novel Class of Cationic Biocides. III. Immobilization of Phosphonium Salts by Surface Photografting and Antibacterial Activity of the Surface–Treated Polymer Films," *J. Polymer Sci.* 31(6):1467–1472, 1993, Part A: Polymer Chemistry.

Kanazawa, A., et al., "Polymeric Phosphonium Salts as a Novel Class of Cationic Biocides. VI. Antibacterial Activity of Fibers Surface–Treated With Phosphonium Salts Containing Trimethoxysilane Groups," *J. App. Polymer Sci.* 52:641–647, 1994.

Kawata, T., et al., "First Permanently Antibacterial and Deodorant Fibers," *Chem. Fibers International* 48:38–43, 1998.

Kreft, P., et al., "Converting From Chlorine to Chloramines: A Case Study," *J. Am. Water Works Assoc.* 77:38–45, 1985.

Mintz, M.J., et al., "τ–Butyl Hypochlorite," *Org. Syntheses., Coll.* 5:184–187, 1963.

Norman, T.S., et al., "The Use of Chloramines to Prevent Trihalomethane Formation," *J. Am. Water Works Assoc.* 72:176–180, 1980.

Nurdin, N., et al. "Biocidal Polymers Active by Contact. III. Aging of Biocidal Polyurethane Coatings in Water," *J. Am. Water Works Assoc.* 72:176–180, 1980.

Nurdin, N., et al. "Biocidal Polymers Active by Contact. II. Biological Evaluation of Polyurethane Coatings With Pendant Quaternary Ammonium Salts," *J. App. Polymer Sci.* 50:663–670, 1993.

Oh, S.–T., et al., "Synthesis and Biocidal Activities of Polymer. III. Bactericidal Activity of Homopolymer of AcDP and Copolymer of AcD With St," *J. App. Polymer Sci.* 54(6):859–866, 1994.

Oh, S.–T., et al., "Synthesis and Fungicidal Activities of Polymeric Biocides. I. TBZ–Containing Monomer and Polymers," *J. Applied Polymer Sci.* 52(5):583–589, 1994.

Panangala et al., "Inactivation of rotavirus by new polymeric water disinfectants," *J. Virol. Methods* 66:263–268 (1997).

Shull, K.E., "Experience With Chloramines as Primary Disinfectants," *J. Am. Water Works Assoc.* 73:101–104, 1981.

Sun, G., et al., "A New Cyclic N–Halamine Biocidal Polymer," *Ind. Eng. Chem. Res.* 33:168–170, 1994.

Sun, G., et al., "Disinfection of Water by N–Halamine Biocidal Polymers," *Ind. Eng. Chem. Res.* 34:4106–4109, 1995.

Sun, G., et al., "Performance of a New Polymeric Water Disinfectant," *J. Am. Water Res. Assoc.* 32(4):793–797, 1996.

Sun, G., et al., "Preparation of Novel Biocidal N–Halamine Polymers," *J. Bioactive and Compatible Polymers* 10:135–144, 1995.

Tsao, T.–C., et al., "Novel N–Halamine Disinfectant Compounds," *Biotechnol. Prog.* 7:60–66, 1991.

Vogt, C., "Controlling Trihalomethanes While Attaining Disinfection," *J. Am. Water Works Assoc.* 73:33–40, 1981.

Williams, D.E., et al., "Is Free Halogen Necessary for Disinfection?," *App. and Environ. Microbiology* 54(10):2583–2585, 1988.

Wolfe, R.L., et al., "Inorganic Chloramines as Drinking Water Disinfectants: A Review," *J. Am. Water Works Assoc.* 76:74–88, 1984.

Worley, S.D., et al., "The Stability in Water of a New Chloramine Disinfectant," *Water Resources Bulletin* 19(1):97–100, 1983.

Worley, S.D., et al., "Halamine Water Disinfectants," *CRC Critical Reviews in Environmental Control* 18(2):133–175, 1988.

Worley, S.D., et al., "Biocidal Polymers," *Trip* 4(11):364–370, 1996.

Worley, S.D., et al., "Disinfection of Water by N–Halamine Biocidal Polymers," *Water Conditioning & Purification,* 96–100 (Jul., 1997).

\* cited by examiner

BIOCIDAL POLYSTYRENE HYDANTOIN PARTICLES

CROSS-REFERENCE TO RELATED APPLICATION

This application is a continuation of U.S. application Ser. No. 09/948,945, filed on Sep. 6, 2001, now U.S. Pat. No. 6,548,054 which is herein incorporated by reference in its entirety.

FIELD OF THE INVENTION

The present invention relates to the manufacture, product, and method of using a highly crosslinked polystyrene N-halamine biocidal polymer. The biocidal polymer is produced under heterogeneous conditions due to its highly crosslinked nature, and in one instance can have pores.

BACKGROUND OF THE INVENTION

While a variety of biocidal polymers (e.g., quaternary ammonium salts, phosphonium materials, halogenated sulfonamides, and biguanides—see *Trends Polym. Sci.* 4:364 (1996)) have been synthesized and tested for biotidal activity, a relatively new class known as cyclic N-halamines has been shown to have far superior properties including biocidal efficacy, long-term stability, and rechargability once the efficacy has been lost. Such a material is poly-1,3-dichloro-5-methyl-5-(4'-vinylphenyl)hydantoin which is an inexpensive derivative of poly-styrene, and which was first described in U.S. Pat. No. 5,490,983, now incorporated herein by reference. Subsequent disclosures of its biocidal properties for use in disinfecting applications for water filters have recently occurred [see *Ind. Eng. Chem. Res.* 33:168 (1994); *Water Res. Bull.* 32:793 (1996); *Ind. Eng. Chem. Res.* 34:4106 (1995); *J. Virolog. Meth.* 66:263 (1997); *Trends in Polym. Sci.* 4:364 (1996); *Water Cond. & Pur.* 39:96 (1997)]. The polymer is effective against a broad spectrum of pathogens including *Staphylococcus aureus, Pseudomonas aeruginosa, Escherichia coli, Candida albicans, Klebsiella terrigena, Legionella pneumophila* and rotavirus, among others, causing large log reductions in contact times of the order of a few seconds in water disinfectant applications. Furthermore, it is effective at pH values at least in the range 4.5 to 9.0 and at temperatures at least in the range 4° C. to 37° C., and it is capable of action even in water containing heavy chlorine demand caused by bioburden.

This biocidal polymer is insoluble in water and organic compounds and will thus not migrate in liquid media. It is stable for long periods of time in dry storage (a shelf life of at least one year at ambient temperature) and can be produced on an industrial scale. Furthermore, all evidence obtained to date suggests that the material is non-toxic and non-sensitizing to humans and animals upon contact.

A variety of microorganisms such as certain bacteria, fungi, and yeasts are capable of aiding the decomposition of bodily fluids such as urine and blood, or in the formation of biofilms, which produce undesirable odors in otherwise useful commercial products. For example, bacteria such as *Bacterium ammoniagenes* and *Proteus mirabilis* are known to accentuate the decomposition of urea to form noxious ammonia gas through a urease enzyme catalysis mechanism (see for example U.S. Pat. No. 5,992,351). The same polymer mentioned above (poly-1,3-dichloro-5methyl-5-(4'-vinylphenyl)hydantoin) has been shown to be effective at inactivating *Proteus mirabilis* and thus minimizing the undesirable odor created by ammonia gas (U.S. patent application Ser. No. 09/685,963, herein incorporated by reference). Also, the polymer is insoluble in bodily fluids so as not to migrate to skin surfaces, rendering it useful, in applications such as disposable diapers, incontinence pads, bandages, sanitary napkins, and pantiliners.

However, the composition of poly-1,3-dichloro-5-methyl-5-(4'-vinylphenyl)hydantoin and use as a biocide for water-filter applications described in U.S. Pat. No. 5,490,983 and its use for odor control described in U.S. patent application Ser. No. 09/685,963 involved a form of the material which was a fine powder with a noticeable chlorine odor. In this form the material exhibited a tendency to cause excessive back-pressure in a water filtration application thereby slowing down flow rates, and the fine particles could potentially be aerosolized in an industrial setting causing concern for workers handling the material. Thus it was deemed necessary to find a method of creating the material as larger particles with less chlorine outgassing, while maintaining its biocidal efficacy.

SUMMARY OF THE INVENTION

The present invention relates to the manufacture, product and the use of novel highly crosslinked biocidal hydantoins in water and air filters and mixed with, absorbent materials or as a coating for the prevention of noxious odors caused by the decomposition of organic materials contained in bodily fluids, on carpets and textile fibers, and in air filters or the like.

One embodiment of the invention is directed to a novel method of making highly crosslinked biocidal hydantoins from highly crosslinked polystyrene. A suitable amount of crosslinking is greater than 5%. In this form, the hydantoin is manufactured as particles rather than as a fine, powder. In one embodiment the particle can include pores to increase the biocidal efficiency. Because of the highly crosslinked nature of the polymer, the reactions can proceed under heterogeneous conditions. In another embodiment the halogen loading can be controlled by either adjusting the pH or the halogen concentration during the halogenation step.

Another aspect of the invention is a novel highly crosslinked biocidal hydantoin. The hydantoin has polymeric chains having the following chemical formula:

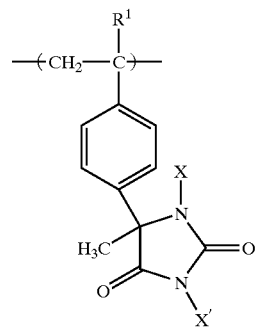

wherein,

X and X' are independently chlorine (Cl), bromine (Br), or hydrogen (H), provided that at least one of X and X' is Cl or Br; and $R^1$ is H or methyl ($CH_3$). The amount of crosslinking is greater than 5%. In one embodiment of the invention, the hydantoin can be provided as a particle, wherein the particle shape is in the form of a bead. However, other embodiments can provide highly crosslinked hydantoin in any other shape.

In one instance the bead is greater than 100 μm or from about 100 μm to about 1200 μm. In another embodiment, the present invention can have pores, wherein the average of the pore size is greater than about 10 nm or from about 10 nm to 100 nm. The biocidal hydantoin made in accordance with the invention has novel highly crosslinked N-halamine polymers of poly-1,3-dihalo-5-methyl-5-(4'-vinylphenyl) hydantoin, poly-1-halo-5-methyl-5-(4'-vinylphenyl) hydantoin, and the alkali salt derivative of the monohalo species, and mixtures thereof, wherein the halogen can be either chlorine or bromine.

A biocidal particle made in accordance with the invention can be used in ways to provide numerous advantages. By providing a plurality of biocidal particles into a collection, such as a filter device, a suitable method of inactivating pathogenic microorganisms and viruses contained in water or air streams by contacting the water or air streams with the filters is provided. The biocidal particles, or beads, will prevent or minimize noxious odors by inactivating microorganisms upon contact which enhance, through catalytic enzymology, the decomposition of organic matter in bodily fluids to ammonia or other noxious materials. In one instance, the biocidal beads can be mixed with an absorbent material to form a mixture. The mixture is then introduced into any article that will contact bodily fluids and the mixture will inactivate halogen sensitive organisms. A biocidal bead made in accordance with the invention, prevents or minimizes noxious odors on air filters by inactivation of microorganisms such as those which cause mildew and molds, as well as those odors emanating from any liquid or aerosol which might contact the surface of the beads.

DETAILED DESCRIPTION OF THE PREFERRED EMBODIMENT

The present invention may be understood more readily by reference to the following detailed description of specific embodiments and the examples included therein.

As used herein, "biocidal polymer" refers to the novel N-halamine polymers named poly-1,3-dihalo-5-methyl-5-(4'-vinylphenyl)hydantoin, poly-1-halo-5-methyl-5-(4'-vinylphenyl)hydantoin, and the alkali salt derivative of the monohalo species, and mixtures thereof, wherein the halogen can be either chlorine or bromine, although this is not meant to be limiting, as any other insoluble N-halamine polymer beads, porous or nonporous, could provide some degree of disinfection and odor-limiting capacity.

As used herein, "bead," in singular or plural, refers to highly crosslinked polystyrene polymers or their reacted products. Beads can be of any size or shape, including spheres so as to resemble beads, but may also include irregularly shaped particles. "Bead" is used interchangeably with particle.

One aspect of the invention relates to the synthesis of the first intermediate poly-4-vinylacetophenone, useful in creating highly crosslinked halogenated hydantoins, using in one instance, porous beads of highly crosslinked polystyrene as the starting material for the Friedel-Crafts acylation procedure. However, any other highly crosslinked polystyrene polymer is suitable. Previously, the polystyrene employed in this reaction step contained minimal crosslinking such that it was soluble in Friedel-Crafts solvents such as carbon disulfide (U.S. Pat. No. 5,490,983). Since chemical reactions generally proceed best when all reactants are dissolved in a solvent to ensure maximum contact of the reactants, it was unexpected that the heterogeneous reaction of the highly crosslinked poly-styrene beads, which were insoluble in carbon disulfide, would react well with acetyl chloride under Friedel-Crafts conditions to produce beads in which the poly-4-vinylacetophenone was formed throughout the porous beads.

Another aspect of the invention relates to the heterogeneous reaction of the poly-4-vinylacetophenone beads with ammonium carbonate and (sodium or potassium) cyanide to produce beads having poly-5-methyl-5-(4'-vinylphenyl) hydantoin throughout their porous structure useful in creating the highly crosslinked halogenated hydantoins. Previously (U.S. Pat. No. 5,490,983), the minimally crosslinked poly-4-vinylacetophenone was dissolved in a solvent such as an ethanol/water mix for this step which led to the formation of a product composed of a fine powder. Again, it was unexpected that the reaction could be made to proceed efficiently with the undissolved porous beads leading to a product having particle size similar to that of the highly crosslinked poly-styrene beads.

Another aspect of the invention relates to the heterogeneous halogenation of the poly-5-methyl-5-(4'-vinylphenyl) hydantoin porous beads so as to produce either poly-1,3-dichloro-5-methyl-5-(4'-vinylphenyl)hydantoin or poly-1,3-dibromo-5-methyl-5-(4'-vinylphenyl)hydantoin or their monohalo derivatives (either protonated or as their alkali metal salts) or any mixture thereof, as beads, which are biocidal and maintain a particle size similar to the starting crosslinked poly-styrene beads.

Another aspect of the invention relates to control of the amount of biocidal halogen covalently bonded to the hydantoin rings on the beads by use of halogen reagent concentration control and/or of pH adjustments.

Another aspect of the invention relates to the use of poly-1,3-dichloro-5-methyl-5-(4'-vinylphenyl)hydantoin and poly-1,3-dibromo-5-methyl-5-(4'-vinylphenyl) hydantoin beads and their monohalo derivatives (either protonated or as their alkali metal salts) and mixtures thereof for inactivation of pathogenic microorganisms and viruses in water and air disinfection applications and for inactivation of organisms causing noxious odors.

Another aspect of the invention is directed to a highly crosslinked biocidal bead having the following chemical formula:

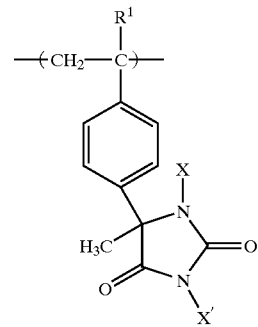

wherein,

X, and X' are independently chlorine, bromine, hydrogen, provided that at least one of X and X' is chlorine or bromine, and $R^1$ is hydrogen or methyl. The novelty of the biocidal bead is the starting compound used which is highly crosslinked polystyrene having greater than 5% crosslinking. Such starting polystyrene polymers are well known to those in the art. However, their use in making the biocidal compounds of the present invention has heretofore been unknown. In one embodiment of a bead made according to the invention, the bead contains pores.

The present invention also relates to the use of a novel highly crosslinked, porous N-halamine biocidal polymer for the purpose of inactivating pathogenic microorganisms and viruses in water and air filtration applications, thereby rendering the water and/or air safe for human consumption. It also relates to the use of the same polymer for inactivating microorganisms such as bacteria, fungi, and yeasts which can cause noxious odors in commercial products such as disposable diapers, incontinence pads, bandages, sanitary napkins, pantiliners, sponges, mattress covers, shoe inserts, animal litter, carpets, fabrics, and air filters, thereby rendering the products free of noxious odors under normal use conditions.

The biocidal polymer beads to be used in this invention will be employed in one instance, in a cartridge filter application for water or air disinfection. The biocidal polymer beads can, for example, be mixed with an absorbent material wherein, the biocidal polymer weight percentage is about 0.1 to 5.0, or about 1.0, for applications involving bodily fluids such as disposable diapers, incontinence pads, bandages, sanitary napkins, pantiliners, mattress covers, shoe inserts, sponges, and animal litter. For air filters, coating techniques, or simple embedment of particles of the biocidal polymer into available filter material, a weight percentage of about 0.1 to 2.0, or about 0.5 to 1.0, can be employed. However, any amount of biocidal polymer made in accordance with this invention will realize beneficial biocidal activity.

The mechanism by which the biocidal polymer realizes biocidal activity is believed to be a result of surface contact of the organism with chlorine or bromine moieties covalently bound to the hydantoin functional groups of the polymer. The chlorine or bromine atoms are transferred to the cells of the microorganisms where they cause inactivation through a mechanism not completely understood, but probably involving oxidation of essential groups contained within the enzymes comprising the organisms.

It is contemplated that a wide variety of filtration devices, such as cartridges or sandwich cakes and the like can be used in conjunction with the biocidal polymer beads made according to the invention, from very large units in small water treatment plants and in the air-handling systems of large aircraft, hotels, and convention centers, to small filters as might be employed in household carafes and for faucets and portable devices for backpacking and military field use. It is further contemplated that a broad variety of absorbent and filler materials can be used in conjunction with the biocidal polymer to aid in preventing noxious odors. Suitably, such materials will enable the contact of the biocidal particles with the medium carrying the microorganisms, such as fluids, aerosol particles, and solid contaminants for sufficient periods of time such that the biocidal polymer particles can make surface contact with the odor-causing microorganisms, in addition to their usual absorptive functions. Such materials include, but are not limited to: swellable clays, zeolites, alumina, silica, cellulose, wood pulp, and super absorbent polymers. The odor control material could contain further adjuvants such as deodorants, fragrances, pigments, dyes, and mixtures of these for cosmetic purposes.

A marked advantage of the biocidal polymer beads of this invention over prior odor-controlling technology is that they are a much more effective biocide against pathogenic microorganisms encountered in medical applications such as *S. aureus* and *P. aeruginosa* than are commercial biocides such as the quaternary ammonium salts, so they can serve a dual function, i.e., inactivation of odor-causing microorganisms and disease-causing pathogens. For this reason they will have wide-spread use in hospital settings.

It should be understood that the practice of this invention applies to odors generated by both human and animal fluids as well as to airborne and waterborne organisms.

It should be emphasized that the biocidal polymer particle made in accordance with the invention can be created in a variety of sizes or shapes dependent upon the particle size or shape of the starting highly crosslinked polystyrene material. In one instance the beads are porous to some degree allowing more efficient heterogeneous reactions to be performed upon them, although nonporous beads could be used also with concomitant lower biocidal efficacy. For the applications contemplated herein, the particle size of the biocidal polymer bead can be in the range of about 100 to 1200 $\mu$m, or in the range of about 300 to 800 $\mu$m. This particle size provides adequate flow characteristics for microbiologically contaminated fluids and no risk of exposure of the respiratory systems of workers to fine aerosolized particles. These two factors are a marked improvement over the powder versions of poly-1,3-dichloro-5-methyl-5-(4'-vinylphenyl) hydantoin or poly-1,3-dibromo-5-methyl-5-(4'-vinylphenyl) hydantoin disclosed in U.S. Pat. No. 5,490,983 and use for odor control as described in U.S. patent application Ser. No. 09/685,963. For the applications contemplated herein the biocidal polymer beads can have pore sizes in the range of about 10 to 100 nm, or in the range of about 30 to 70 nm. A porous structure provides additional surface area for heterogeneous reaction steps, since the highly crosslinked beads are insoluble in organic solvents and water. Suitably, the degree of crosslinking of the starting poly-styrene material should be in the range of about 3 to 10 weight percent to insure hardness and lack of solubility, or about 5 to 8 weight percent, or even greater than 3% or greater than 5%. Non-limiting examples of highly crosslinked, porous polystyrene beads which could be used in one aspect in accordance with this invention are obtained from Suqing Group (Jiangyin, Jiangsu; PRC) or from the Purolite Company (Philadelphia, Pa.).

In accordance with one aspect of the invention to make highly crosslinked biocidal hydantoin, a first step involves the suspension of highly crosslinked, porous poly-styrene beads in a Friedel-Crafts solvent, such as carbon disulfide, methylene chloride, an excess amount of acetyl chloride and the like and then reacted with acetyl chloride or acetic anhydride and the like in the presence of aluminum chloride, or gallium chloride and the like under reflux conditions. The isolated product, poly-4-vinylacetophenone beads, is purified by exposure to ice/HCl and then boiling water. The second reaction step in accordance with this invention includes reacting the pure poly-4-vinylacetophenone beads with potassium cyanide or sodium cyanide and ammonium carbonate or any source of gaseous ammonia in an ethanol/water mixture and the like solvent in a high pressure reactor suitable to contain the gaseous ammonia produced from the ammonium carbonate, which in one instance is run at about 85° C., while the pressure is allowed to vary with the amount of ammonia produced. Thusly, producing poly-5-methyl-5-(4'-vinylphenyl)hydantoin beads, which can be purified by exposure to boiling water rinses. The third reaction step in accordance with this invention includes the syntheses of the biocidal polymer beads (poly-1,3-dichloro-5-methyl-5-(4'-vinylphenyl)hydantoin or poly-1,3-dibromo-5-methyl-5-(4'-vinylphenyl)hydantoin) or their monohalo protonated or alkali metal salt derivatives by exposure of the poly-5-methyl-5-(4'-vinylphenyl)hydantoin beads to a source of free chlorine (e.g., gaseous chlorine, sodium hypochlorite, calcium hypochlorite, sodium dichloroisocyanurate, etc.) or free bromine (e.g., liquid bromine, sodium bromide/potassium peroxymonosulfate, etc.) in an aqueous base. If chlorine gas is used, the reactor should be chilled to about 10° C. to minimize undesirable side reactions. Ambient temperature can be employed for the other sources of free halogen, and the reactions can be carried out in a reactor or in situ in a cartridge filter packed with the unhalogenated precursor. Optionally, the percent halogen on the polymer beads can be controlled by pH adjustments. For example, at pH 6–7 maximum halogenation is achieved; whereas, at pH near 12 a monohalogenated alkali metal salt is obtained. Intermediate pH's (7–11) provide mixtures of dihalo and monohalo derivatives. The pH adjustments can be made using acids such as hydrochloric or acetic or bases such as sodium hydroxide or sodium carbonate. Higher free chlorine contents of greater than 14% chlorine by weight are suitable for water or air disinfection applications; whereas, the monohalo derivative or its alkali metal salt is adequate for odor control applications. On the other hand, bromine contents of greater than 34% are suitable for water disinfection applications. But because of outgassing, bromine, at these high concentrations, may be less suitable for air applications.

The present invention is more particularly described in the following examples which are intended as illustrative only since numerous modifications and variations therein will be apparent to those skilled in the art.

EXAMPLE 1

Preparation of Chlorinated Beads at Maximum Chlorine Loading

Porous beads of 5.6% crosslinked polystyrene obtained from Suqing Group (Jiangyin, Jiangsu, PRC) having particle sizes in the range 250 to 600 $\mu$m and pore sizes of about 50 nm were cleaned by soaking in acetone for 2 hours at 25° C. and passing 2 portions of acetone through the beads in a filter funnel. Following drying to constant weight in air at 25° C., 50 g of the beads were suspended in 300 mL of carbon disulfide in a 500 mL flask and allowed to swell for 15 minutes. Then 128.2 g of anhydrous aluminum chloride were added, and the mixture was stirred for 15 minutes at 25° C. While continuously stirring, a mixture of 59 g of acetyl chloride and 50 mL of carbon disulfide was slowly added to the flask from a dropping funnel over a period of 2 hours with the temperature being held at 25° C. The mixture was refluxed for a period of 2 hours. The product of the reaction was poly-4-vinylacetophenone porous beads. Purification steps included exposure to 600 mL of an ice/HCl mixture (2 parts ice/1 part HCl by weight), then 5 portions of 600 mL of boiling water for 15 minute increments, and then suction filtration. The product in the filter funnel was washed continuously with boiling water until the filtrate became clear of color, and finally the product was dried to constant weight at 80° C. The yield was 64.4 g of white poly-4-vinylacetophenone porous beads; an infrared spectrum of a small sample of the beads (crushed to a powder) in a KBr pellet exhibited prominent bands at 1601 and 1681 cm$^{-1}$ in good agreement with that of the powdered poly-4-vinylacetophenone disclosed in U.S. Pat. No. 5,490,983 indicative of an efficient heterogeneous Friedel-Crafts reaction with the insoluble, highly crosslinked, porous polystyrene beads.

Then 3.65 g of the porous poly-4-vinylacetophenone beads, 4.5 g of potassium cyanide, 14.4 g of ammonium carbonate, and 80 mL of ethanol/water (1:1 volume ratio) were placed in a 300 mL Parr high-pressure reactor. The mixture was reacted while stirring at 85° C. for 14 hours. The product (poly-5-methyl-5-(4'-vinylphenylhydantoin) porous beads) was purified by exposure to boiling water for 5 increments of 15 minutes each, and then to flowing boiling water in a filter funnel until the filtrate was colorless. The beads were then air-dried at 80° C. until their weight became constant. The yield was 4.95 g of white poly-5-methyl-5-(4'-vinylphenyl)hydantoin porous beads; an infrared spectrum of a small sample of the beads (crushed to a powder) in a KBr pellet exhibited prominent bands at 1510, 1725, and 1778 cm$^{-1}$ in good agreement with that of the powdered poly-5-methyl-5-(4'-vinylphenyl)hydantoin disclosed in U.S. Pat. No. 5,490,983 indicative of an efficient heterogeneous reaction with the insoluble, highly crosslinked, porous poly-4-vinylacetophenone beads.

Then 5.0 g of the poly-5-methyl-5-(4'-vinylphenyl)hydantoin porous beads were suspended in a flask containing 90 mL of 1 N sodium hydroxide, and chlorine gas was slowly bubbled into the suspension held at 10° C. until the solution became saturated (green) with free chlorine. The mixture was stirred for 1.5 hours at 25° C. without the further addition of chlorine gas. The beads were filtered and washed with 5 portions of 50 mL of water and dried in air. The yield was 6.5 g of light yellow, porous poly-1,3-dichloro-5-methyl-5-(4'-vinylphenyl)hydantoin beads; an infrared spectrum of a small sample of the beads (crushed to a powder) in a KBr pellet exhibited prominent bands at 1756 and 1807 cm$^{-1}$ in good agreement with that of the powdered poly-1,3-dichloro-5-methyl-5-(4'-vinylphenyl)hydantoin disclosed in U.S. Pat. No. 5,490,983 indicative of an efficient heterogeneous reaction of chlorine with the insoluble, highly crosslinked, porous poly-5-methyl-5-(4'-vinylphenyl)hydantoin beads. An iodometric/thiosulfate titration of weighed, crushed beads indicated that the beads contained 20.0 weight percent chlorine. Furthermore, the beads retained their shapes throughout the three reaction steps and increased somewhat in size (to 400–800 $\mu$m) due to swelling.

EXAMPLE 2

Biocidal Efficacies of Chlorinated Beads at Maximum Chlorine Loading

The beads as prepared in Example 1 were tested for biocidal activity against several pathogens contained in water. In one test, about 3.9 g of chlorinated beads were packed into a glass column having inside diameter 1.3 cm to a length of about 7.6 cm; the empty bed volume was 3.3 mL. An identical sample column of unchlorinated beads was prepared to be used as a control. After washing the column with demand-free water until less than 0.2 mg/L of free chlorine could be detected in the effluent, an aqueous solution of 50 mL of pH 7.0 phosphate-buffered, demand-free water containing $6.9 \times 10^6$ CFU (colony forming units)/mL of the Gram positive bacterium *Staphylococcus aureus* (ATCC 6538) was pumped through the column at a measured flow rate of about 3.0 mL/second. The effluent was quenched with 0.02 N sodium thiosulfate before plating. All of the bacteria were inactivated in one pass through the column, i.e., a 6.9 log reduction in a contact time of less than or equal to 1.1 seconds. The same result was achieved with the Gram negative bacterium 0157:H7 *Escherichia coli* (ATCC 43895) at a concentration of $8.5 \times 10^6$ CFU/mL, i.e., a 7.0 log reduction in a contact time of less than or equal to 1.1 seconds. The control column containing unhalogenated beads gave no reduction of either bacterium in a contact time of 1.6 seconds when the same concentrations of the inoculums were employed.

The results in this example indicate that fully chlorinated poly-1,3-dichloro-5-methyl-5-(4'-vinylphenyl)hydantoin porous beads possess considerable efficacy against a variety of pathogens in aqueous solution and should be excellent for disinfecting water-containing same.

EXAMPLE 3

Preparation and Biocidal Efficacy Testing of Brominated Beads 5.0 g of poly-5-methyl-5-(4'-vinylphenyl)hydantoin porous beads prepared as described in Example 1 were suspended in a flask containing 50 mL of 2 N NaOH. While stirring the suspension, 10.0 g of liquid bromine were added dropwise at 25° C. over a period of 10 minutes. The pH was adjusted to 6.4 by the addition of 4 N acetic acid, and the mixture was stirred at 25° C. without the further addition of bromine for 1 hour. The brominated beads were then filtered and washed 5 times with 100 mL portions of tap water and dried in air at 25° C. for 8 hours. An iodometric/thiosulfate titration indicated that the beads contained a 36.8 percent loading of bromine by weight. An infrared spectrum of a small sample of the beads (crushed to a powder) in a KBr pellet exhibited prominent bands at 1724 and 1779 cm$^{-1}$ in good agreement with that of powdered poly-1,3-dibromo-5-methyl-5-(4'-vinylphenyl)hydantoin prepared earlier starting from soluble poly-styrene pellets, indicative of an efficient heterogeneous reaction of bromine with the insoluble, highly crosslinked, porous poly-5-methyl-5-(4'-vinylphenyl)hydantoin beads. A weak band at 1602 cm$^{-1}$ indicative of the presence of a small amount of monobrominated sodium salt was also observed. This band becomes the dominant one (indicating that the predominant product is the monobromo sodium salt) when the bromination reaction is performed at pH 8.5.

A column packed with the highly brominated beads (empty bed volume of 3.1 mL) similar to those described in Example 2 was prepared. After washing the column with demand-free water until less than 1 mg/L of free bromine could be detected in the effluent, an aqueous solution of 50 mL of pH 7.0 phosphate-buffered, demand-free water containing 6.9×10$^6$ CFU (colony forming units)/mL of the Gram positive bacterium *Staphylococcus aureus* (ATCC 6538) was pumped through the column at a measured flow rate of about 3.0 mL/second. The effluent was quenched with 0.02 N sodium thiosulfate before plating. All of the bacteria were inactivated in one pass through the column, i.e., a 6.9 log reduction in a contact time of less than or equal to 1.0 second. The same result was achieved with the Gram negative bacterium 0157:H7 *Escherichia coli* (ATCC 43895) at a concentration of 8.5×10$^6$ CFU/mL, i.e., a 7.0 log reduction in a contact time of less than or equal to 1.1 second. The control column containing unhalogenated beads gave no reduction of either bacterium in a contact time of 1.6 seconds when the same concentrations of the inoculums were employed.

The results in this example indicate that fully brominated poly-1,3-dibromo-5-methyl-5-(4'-vinylphenyl)hydantoin porous beads possess considerable efficacy against both Gram positive and Gram negative bacteria in aqueous solution and should be excellent for disinfecting water-containing same.

EXAMPLE 4

Control of Chlorine Loading on the Porous Beads

A series of experiments were performed to establish means of controlling halogen loading on the porous poly-5-methyl-5-(4'-vinylphenyl)hydantoin beads. In these experiments the loading was controlled by two means—adjustment of the concentration of halogen added to and adjustment of the pH of the suspension of the porous poly-5-methyl-5-(4'-vinylphenyl)hydantoin beads.

A method of producing beads with a very high chlorine loading (about 20% by weight) which employed gaseous chlorination was discussed in Example 1. The infrared spectrum of those beads (crushed to a powder) in a KBr pellet exhibited prominent bands at 1756 and 1807 cm$^{-1}$, and no prominent band near 1600 cm$^{-1}$ indicative of a monochlorinated sodium salt, meaning the hydantoin ring contained chlorine atoms bonded to both of its nitrogens.

Beads having chlorine loadings of about 17% by weight were prepared by either of two methods. In one procedure 2.2 g of porous poly-5-methyl-5-(4'-vinylphenyl)hydantoin beads were suspended in 15 mL of industrial grade sodium hypochlorite (12.5% NaOCl) and 15 mL of water. The pH of the solution was adjusted to about 8.0 by addition of 2 N HCl. This suspension was stirred at 25° C. for 1 hour, filtered, washed 5 times with 50 mL portions of water, and dried in air for 8 hours. A iodometric/thiosulfate titration indicated that the chlorine loading was 16.9% by weight. The infrared spectrum of the beads (crushed to a powder) in a KBr pellet exhibited prominent bands at 1751 and 1805 cm$^{-1}$, and a weak band near 1609 cm$^{-1}$, indicative of primarily the dichloro derivative, but that a small amount of the monochlorinated sodium salt was present. When the same technique was employed, with the exception that the pH was only lowered to 8.8 using HCl, the titrated chlorine content was only 13.3% by weight, and the infrared spectrum then contained prominent bands at 1602, 1731, and 1801 cm$^{-1}$; the two low frequency bands had similar intensities indicating a mixture of the dichloro derivative and a substantial amount of the monochloro sodium salt. In the other procedure, the beads were first chlorinated to high loading, and then treated with base which caused partial formation of the sodium salt. 8.1 g of porous poly-5-methyl-5-(4'-vinylphenyl)hydantoin beads were suspended in 50 mL of industrial grade sodium hypochlorite (12.5% NaOCl) and 100 mL of water. The pH, of the solution was adjusted to about 6.5 by addition of 2 N HCl. This suspension was stirred at 25° C. for 1 hour, filtered, washed 5 times with 100 mL portions of water, and dried in air for 8 hours. A iodometric/thiosulfate titration indicated that the chlorine loading was 19.0% by weight. The infrared spectrum of the beads (crushed to a powder) in a KBr pellet exhibited prominent bands at 1751 and 1806 cm$^{-1}$, and almost no band near 1600 cm$^{-1}$, indicative of primarily the dichloro'derivative. Then 2.8 g of these beads were soaked in 60 mL of 0.05 N NaOH at 25° C. for 5 minutes, filtered, washed with 50 mL portions of water 5 times, and dried in air for 8 hours. This treatment caused a decline in chlorine loading to 15.5% by weight (IR bands at 1601, 1749, and 1804 cm$^{-1}$). The 1601cm$^{-1}$ band had moderate intensity, but was weaker than for the sample discussed above having only 13.3% chlorine loading, indicative of a lesser proportion of monochlorinated sodium salt for this sample. Finally, when 1.0 g of the same material (19.0% by weight chlorine loading) was soaked in 100 mL of saturated NaHCO$_3$, which is a much weaker base than NaOH, for 40 minutes at, 25° C., then filtered, washed 5 times with 50 mL portions of water, and dried in air for 8 hours, the resulting beads contained a chlorine loading of 17.3% by weight (IR bands at 1607 (weak), 1751 (strong), and 1806 (moderate)cm$^{-1}$) indicative of beads containing primarily the dichloro derivative, but some of the monochloro sodium salt.

Beads having chlorine loadings of about 10% by weight can also be prepared by two methods. In one procedure, 2.8 g of the porous poly-5-methyl-5-(4'-vinylphenyl)hydantoin beads chlorinated at pH 6.5 (to produce a chlorine loading of 19.0% by weight) were soaked in 60 mL of 0.05 N NaOH for 20 minutes at 25° C., then filtered, washed 5 times with 50 mL portions of water, and dried in air for 8 hours. The resulting beads contained a chlorine loading of 10.8% by weight (IR bands at 1599 (very strong), 1728 (moderate), and 1784 (weak)$cm^{-1}$) indicative of beads containing primarily the monochloro sodium salt, but some of, the dichloro derivative. In the other procedure, 6.2 g of the porous poly-5-methyl-5-(4'-vinylphenyl)hydantoin beads were stirred with 50 mL of industrial 12.5% by weight NaOCl and 100 mL of water without pH adjustment (the pH of the suspension was 12.5) for 45 minutes (a similar result occurs in 5 minutes) at 25° C. Then the beads were filtered, washed 5 times with 50 mL portions of water, and dried in air for 8 hours. The resulting beads contained a chlorine loading of 10.3% by weight (IR bands at 1598 (very strong), 1724 (moderate), and 1784 (weak)$cm^{-1}$) indicative of beads containing primarily the monochloro sodium salt, but some of the dichloro derivative as in the first procedure. Even with a large stoichiometric excess of free chlorine from NaOCl, the beads were only chlorinated to the 10.3% level at the natural highly basic pH of the suspension. For higher chlorine loadings, downward pH adjustment is necessary.

Beads having chlorine loadings lower than about 10% by weight can be prepared by lowering the amount of free chlorine available for reaction with them. For example, 1.0 g samples of the porous poly-5-methyl-5-(4'-vinylphenyl)hydantoin beads were reacted with stirring with 3 different volumes of saturated calcium hypochlorite (1165 mg/L free $Cl^+$) for 1 hour each at 25° C. Following filtration, washing with water, and drying in air, the samples were titrated for chlorine content. The results were (mL of $Ca(OCl)_2$ solution, % Cl by weight): 100, 6.8%; 150, 9.8%; 200, 10.2%. The infrared spectrum of the sample giving the 6.8% by weight loading contained a very strong band at 1596 $cm^{-1}$ attributable to the calcium salt of the monochlorinated derivative and prominent bands at 1728 and 1782 $cm^{-1}$ which may be attributed to unreacted poly-5-methyl-5-(4'-vinylphenyl)hydantoin. Similar results were obtained when a less than stoichiometric amount of NaOCl was used as the source of free chlorine.

It is possible to convert any sodium salt of the monochloro derivative present to its protonated form (porous poly-1-chloro-5-methyl-5-(4'-vinylphenyl)hydantoin beads) by addition of dilute acid after isolation of the salt. For example, 3.2 g of the beads having 10.3% by weight chlorine discussed above were immersed in 50 mL of 0.6 N HCl for 3 minutes with stirring at 25° C. Following filtration, washing 5 times with 50 mL portions of water, and drying in air for 8 hours at 25° C., a sample was titrated, and found to contain a chlorine loading of 10.8% by weight. The infrared spectrum of the crushed beads now contained prominent bands at 1730 and 1791 $cm^{-1}$, but the intense, broad band found at 1598 $cm^{-1}$ for the monochlorinated sodium salt disappeared leaving only a weak, sharp band at 1607x $cm^{-1}$ attributable to the aromatic rings of the polystyrene backbone.

Thus the weight percent halogen contained in the biocidal porous beads can be controlled by regulating the amount of halogen added and/or by controlling the pH of the aqueous suspension of the porous poly-5-methyl-5-(4'-vinylphenyl)hydantoin beads. Also, the monochloro derivative can be isolated as an alkali metal salt upon treatment with base, or as the protonated analog upon treatment with acid. The form of the final product is important as relates to the intended application. For water disinfection applications, weight percent chlorine in the range of 10 to 17% is generally needed; whereas, for odor control applications, weight percent chlorine in the range of 6 to 10% is sufficient.

EXAMPLE 5

The Biocidal Efficacies of the Beads Containing Medium and Low Chlorine Loadings Efficacies of the porous beads containing medium and low chlorine loadings against the bacterium *S. aureus* (ATCC 6538) were determined using a column test as described in Example 2. 3.11 g of the beads which were primarily the monochlorinated sodium salt (10.2% by weight chlorine) with empty bed volume of 4.10 mL were challenged with 50 mL of *S. aureus* at a concentration of about $1.1 \times 10^7$ CFU/mL at a flow rate of 2.9 mL/second. A complete 7.1 log reduction was observed to occur in a contact time interval of 1.4 to 2.8 seconds. For 3.02 g of the beads which were primarily the monochlorinated calcium salt (6.8% by weight chlorine) with empty bed volume of 4.39 mL, a challenge with 50 mL of *S. aureus* at a concentration of about $1.3 \times 10^7$ CFU/mL at a flow rate of 3.0 mL/second, a complete 7.2 log reduction was observed to occur in a contact time interval of 1.5 to 3.0 seconds. For 3.06 g of the beads which were primarily the monochlorinated protonated derivative (10.5% by weight chlorine) with empty bed volume of 3.84 mL, a challenge with 50 mL of *S. aureus* at a concentration of about $1.1 \times 10^7$ CFU/mL at a flow rate of 3.0 mL/second, provided a complete 7.1 log reduction in a contact time of less than or equal to 1.3 seconds. Thus, the monochloro alkali metal salt beads at medium and low chlorine loadings are still biocidal in short contact times, although not quite as efficacious as the beads with high chlorine loadings discussed in Example 2. Also, the protonated forms of these beads are biocidal in somewhat shorter contact times than are their alkali metal analogs.

EXAMPLE 6

Beads Having Higher Degree of Crosslinking

Porous beads of 8.0% crosslinked polystyrene obtained from Purolite Company (Philadelphia, Pa.) having particle sizes in the range 350 to 950 µm and pore sizes in the range 20 to 40 nm were used without precleaning. 20.8 g of the beads were suspended in 150 mL of carbon disulfide and allowed to swell for 15 minutes at 25° C. Then 53.4 g of anhydrous aluminum chloride were added, and the mixture was stirred for 15 minutes at 25° C. While continuously stirring, 23.6 g of acetyl chloride were slowly added to the flask from a dropping funnel over a period of 45 minutes with the temperature being held at 25° C. The mixture was refluxed for a period of 2 hours. The product of the reaction was poly-4-vinylacetophenone porous beads. Purification steps included exposure to 600 mL of an ice/HCl mixture (2 parts ice/1 part HCl by weight), then 5 portions of 600 mL of boiling water for 15 minute increments, and then suction filtration. The product in the filter funnel was washed continuously with boiling water until the filtrate became clear of color, and finally it was dried to constant weight at 80° C. The yield was 26.5 g of white poly-4-vinylacetophenone porous beads; an infrared spectrum of a small sample of the beads (crushed to a powder) in a KBr pellet exhibited prominent bands at 1604 and 1683 $cm^{-1}$ in good agreement with that of the powdered poly-4- vinylacetophenone disclosed in U.S. Pat. No. 5,490,983 indicative of an efficient heterogeneous Friedel-Crafts reaction with the insoluble, highly crosslinked, porous polystyrene beads.

Then 11.0 g of the porous poly-4-vinylacetophenone beads, 13.5 g of potassium cyanide, 43.2 g of ammonium carbonate, and 120 mL of ethanol/water (1:1 volume ratio) were placed in a 300 mL Parr high-pressure reactor. The mixture was reacted while stirring at 85° C. for 14 hours. The product (poly-5-methyl-5-(4'-vinylphenylhydantoin) porous beads) was purified by exposure to boiling water for 5 increments of 15 minutes each, and then to flowing boiling water in a filter funnel until the filtrate was colorless. The beads were then air-dried at 80° C. until their weight became constant. The yield was 14.7 g of white poly-5-methyl-5-(4'-vinylphenyl)hydantoin porous beads; an infrared spectrum of a small sample of the beads (crushed to a powder) in a KBr pellet exhibited prominent bands at 1509, 1724, and 1786 $cm^{-1}$ in good agreement with that of the powdered poly45-methyl-5-(4'-vinylphenyl)hydantoin disclosed in U.S. Pat. No. 5,490,983 indicative of an efficient heterogeneous reaction with the insoluble, highly crosslinked, porous poly-4-vinylacetophenone beads.

Then 4.0 g of the poly-5-methyl-5-(4'-vinylphenyl) hydantoin porous beads were suspended in a flask containing 60 mL of water and 30 mL of 12.5% by weight NaOCl; 2 N HCl was used to adjust the pH to 7.8. The mixture was stirred for 1 hour at 25° C., and the beads were filtered and washed with 5 portions of 50 mL of water and dried in air for 8 hours. An infrared spectrum of a small sample of the beads (crushed to a powder) in a KBr pellet exhibited prominent bands at 1749 and 1806$cm^{-1}$ in good agreement with that of the powdered poly-1,3-dichloro-5-methyl-5-(4'-vinylphenyl)hydantoin disclosed in U.S. Pat. No. 5,490,983 indicative of an efficient heterogeneous reaction of chlorine with the insoluble, highly crosslinked, porous poly-5-methyl-5-(4'-vinylphenyl)hydantoin beads. An iodometric/thiosulfate titration of weighed, crushed beads indicated that the beads contained 10.5 weight percent chlorine. The lower percentage of chlorine than found for the beads discussed in Example 1 is indicative of the higher degree of crosslinking in these beads and the presence of some monochlorinated derivative as well as poly-1,3-dichloro-5-methyl-5-(4'-vinylphenyl)hydantoin. The beads retained their shapes throughout the three reaction steps and increased somewhat in size (to 600–800 $\mu$m) due to swelling. When the porous poly-5-methyl-5-(4'-vinylphenyl)hydantoin beads were chlorinated with 12.5% by weight NaOCl without pH adjustment, the titrated chlorine loading was 8.9% by weight, and infrared bands were obtained at 1600 (very strong) and 1718 (moderate)$cm^{-1}$, indicative of the presence of the monochloro sodium salt.

A column test was performed on the 10.5% by weight chlorine beads discussed above. The column was packed with 3.26 g of the beads; the empty bed volume was 2.83 mL. A complete inactivation (6.9 log) of S. aureus (ATCC 6538) was obtained in one pass through the column at a contact time of less than or equal to 1 second. Thus it can be concluded that different degrees of crosslinking and variable particle and pore sizes in the starting poly-styrene can be employed for disinfection with success as long as the crosslinking degree is sufficient to prevent dissolution of the beads at any reaction step.

EXAMPLE 7

Odor Control

Beads prepared as described in Example 4 with different chlorine loadings (16.5% —primarily poly-1,3-dichloro-5-methyl-5-(4'-vinylphenyl)hydantoin; 10.2%—a mixture of the dichloro and sodium salt of the monochloro derivatives; 7.3%—primarily the sodium salt of poly-1chloro-5-methyl-5-(4'-vinylphenyl)hydantoin) were evaluated as to their efficacies in controlling ammonia generation through inactivation of *Proteus mirabilis*.

Blends of 5–10 mg of chlorinated beads and 1.0 g of wood pulp (0.5 or 1.0% by weight beads) were prepared by mixing with 200 mL of distilled water in a blender (Hamilton Beach 7 Blend Master Model 57100, whip setting). Following vacuum filtration, which produced wood-pulp pads, and drying in air at 25° C., the samples were placed in Petri dishes.

An inoculum known to provide a high level of odor was formulated. The formulation included 9 mL of a mixture of 25 mL of pooled human female urine and 1.25 g of urea and 1 mL of an aqueous suspension of 1.3×$10^8$ CFU/mL of *Proteus mirabilis*.

Each sample, including a control of wood pulp with no biocidal polymer, was inoculated with 1 mL of the formulation described above, and the Petri dishes were sealed with paraffin and incubated at 37° C. for 24 hours. The samples were then measured for ammonia production using Drager tubes (Fisher Scientific, Pittsburgh, Pa. and Lab Safety Supply, Janesville, Wis.) capable of detection in the range 0.25 to 30 mg/L. The control sample registered an ammonia concentration greater than 30 mg/L, while all samples (0.5 and 1.0% loadings) containing the chlorinated beads (7.3–16.5%. by weight chlorine) registered ammonia concentrations less than 0.25 mg/L.

It can be concluded that the porous chlorinated beads are highly effective at preventing ammonia generation and hence noxious odor even at very low blends with an absorbent material like wood pulp.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An absorbent article, comprising a polystyrene polymer having pendant hydantoin groups, wherein the polymer is at least 3% crosslinked.

2. The absorbent article of claim 1, wherein the article is one of at least a diaper, an incontinence pad, a bandage, a sanitary napkin, a mattress cover or a pantiliner.

3. The absorbent article of claim 1, wherein at least some of the hydantoin groups are mono-halogenated.

4. The absorbent article of claim 3, wherein the mono-halogenated hydantoin groups have a halogen bonded to the amide nitrogen of the hydantoin group.

5. The absorbant article of claim 3, wherein at least some of the mono-halogenated hydantoin groups have an alkali metal atom bonded to a nitrogen atom of the hydantoin group.

6. The absorbent article of claim 5, wherein the alkali metal is one of at least potassium or sodium.

7. The absorbent article of claim 3, wherein the mono-halogenated hydantoin groups are halogenated with one of at least chlorine or bromine.

8. The absorbent article of claim 1, wherein the polymer comprises 10–17% by weight chlorine, said chlorine bonded to the pendant hydantoin groups.

9. The absorbent article of claim 1, wherein the polymer comprises 6–10% by weight chlorine, said chlorine bonded to the pendant hydantoin groups.

10. The absorbent article of claim 1, further comprising superabsorbent polymer.

11. The absorbent article of claim 1, further comprising wood pulp fibers.

12. The absorbent article of claim 1, comprising mono-halogenated and di-halogenated hydantoin groups.

13. The absorbent article of claim 1, wherein said polymer has units having the formula:

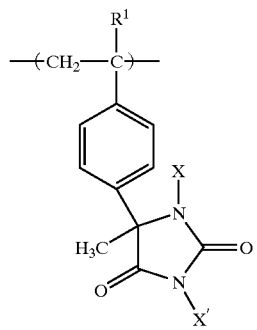

wherein X and X' are independently selected from chlorine, bromine or hydrogen, provided that at least one of X or X' is chlorine or bromine on at least some of the units; and $R^1$ is hydrogen or methyl.

14. An absorbent article, comprising a polystyrene polymer having pendant hydantoin groups, wherein the polymer is at least 5% crosslinked.

15. The absorbent article of claim 14, wherein the article is one of at least a diaper, an incontinence pad, a bandage, a sanitary napkin, a mattress cover or a pantiliner.

16. The absorbent article of claim 14, wherein at least some of the hydantoin groups are mono-halogenated.

17. The absorbent article of claim 14, wherein the mono-halogenated hydantoin groups have a halogen bonded to the amide nitrogen of the hydantoin group.

18. The absorbent article of claim 16, wherein at least some of the mono-halogenated hydantoin groups have an alkali metal atom bonded to a nitrogen atom of the hydantoin group.

19. The absorbent article of claim 18, wherein the alkali metal is one of at least potassium or sodium.

20. The absorbent article of claim 16, wherein the mono-halogenated hydantoin groups are halogenated with at least one of chlorine or bromine.

21. The absorbent article of claim 14, wherein the polymer comprises 10–17% by weight chlorine, said chlorine bonded to the pendant hydantoin groups.

22. The absorbent article of claim 14, wherein the polymer comprises 6–10% by weight chlorine, said chlorine bonded to the pendant hydantoin groups.

23. The absorbent article of claim 14, further comprising superabsorbent polymer.

24. The absorbent article of claim 14, further comprising wood pulp fibers.

25. The absorbent article of claim 14, comprising mono-halogenated and di-halogenated hydantoin groups.

26. The absorbent article of claim 14, wherein said polymer has units having the formula:

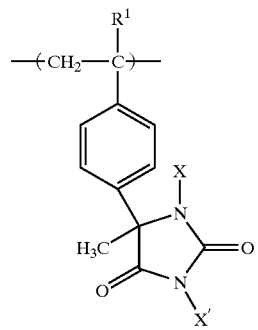

wherein X and X' are independently selected from chlorine, bromine or hydrogen, provided that at least one of X or X' is chlorine or bromine on at least some of the units; and $R^1$ is hydrogen or methyl.

27. An absorbent article, comprising a polystyrene polymer having pendant hydantoin groups, wherein the polymer is at least 8% crosslinked.

28. The absorbent article of claim 27, wherein said polymer has units having the formula:

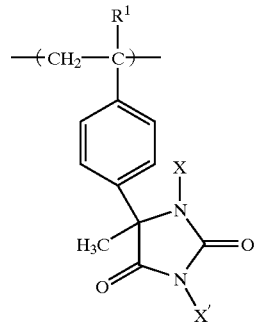

wherein X and X' are independently selected from chlorine, bromine or hydrogen, provided that at least one of X or X' is chlorine or bromine on at least some of the units; and $R^1$ is hydrogen or methyl.

29. The absorbent article of claim 27, further comprising superabsorbent polymer.

30. The absorbent article of claim 27, further comprising wood pulp fibers.

31. The absorbent article of claim 27, wherein the article is one of at least a diaper, an incontinence pad, a bandage, a sanitary napkin, a mattress cover or a pantiliner.

32. An absorbent article, comprising wood pulp fibers and a poly-1-chloro-5-methyl-5-(4'-vinylphenyl)hydantoin.

33. An absorbent article, comprising wood pulp fibers and a poly-1,3-dichloro-5-methyl-5-(4'-vinylphenyl)hydantoin.

34. An antimicrobial product having odor control properties, comprising:

a plurality of fibers; and an amount of a halogenated polystyrene hydantoin effective to control odor caused by a microorganism, wherein the halogenated polystyrene comprises a plurality of repeating units and halogen atoms chemically linked to the repeating units;

each of the repeating units including an amide nitrogen and an imide nitrogen atom;

wherein the majority of the halogen atoms are chemically linked to the amide nitrogen atoms; and wherein the halogenated polystyrene hydantoin is present in an amount from about 0.1% to about 5% by weight based on the total weight of the fibers.

35. An antimicrobial product having odor control properties, comprising:

a plurality of fibers; and an amount of a halogenated polystyrene hydantoin affective to control odor caused by a microorganism, wherein the halogenated polystyrene comprises a plurality of repeating units and halogen atoms chemically linked to the repeating units;

each of the repeating units including an amide nitrogen and an imide nitrogen atom;

wherein at least some of the halogen atoms are chemically linked to the amide nitrogen atom; and wherein the halogenated polystyrene hydantoin is present in an amount from about 0.1% to about 5% by weight based on the total weight of the fibers.

36. An antimicrobial product having odor control properties, comprising:

a plurality of fibers;

halogenated polystyrene polymer having pendent hydantoin groups, wherein the halogenated polystyrene polymer comprises a plurality of repeating units and halogen atoms chemically linked to the repeating units, wherein the polymer is at least 8% crosslinked;

each of the repeating units including an amide nitrogen and an imide nitrogen atom; and wherein at least some of the halogen atoms are chemically linked to the amide nitrogen atoms.

37. The antimicrobial product of claim 36, further comprising superabsorbent polymer.

38. The antimicrobial product of claim 36, further comprising wood pulp fibers.

39. The antimicrobial product of claim 36, wherein the article is one of at least a diaper, an incontinence pad, a bandage, a sanitary napkin, a mattress cover or a pantiliner.

40. The antimicrobial product of claim 34, wherein the halogenated polystyrene hydantoin is present in an amount from about 0.1% to about 1% by weight based on the total weight of the fibers.

41. The antimicrobial product of claim 35, wherein the halogenated polystyrene hydantoin is present in an amount from about 0.1% to about 1% by weight based on the total weight of the fibers.

42. The antimicrobial product of claim 34, wherein the halogenated polystyrene hydantoin is present in an amount from about 0.1% to about 0.5% by weight based on the total weight of the fibers.

43. The antimicrobial product of claim 35, wherein the halogenated polystyrene hydantoin is present in an amount from about 0.1% to about 0.5% by weight based on the total weight of the fibers.

44. A product, comprising a plurality of fibers and a halogenated polystyrene hydantoin effective to control odor caused by a microorganism, wherein the halogenated polystyrene is present in an amount from about 0.1% to about 1% by weight based on the total weight of the fibers.

* * * * *